United States Patent
Chen

(10) Patent No.: US 6,952,840 B2
(45) Date of Patent: Oct. 11, 2005

(54) GOGGLES

(76) Inventor: Chin-Jen Chen, No. 22-9, Liu Kuai Liao, Liu Chia Village, An Ting Hsiang, Tainan Hsien (TW)

( * ) Notice: Subject to any disclaimer, the term of this patent is extended or adjusted under 35 U.S.C. 154(b) by 266 days.

(21) Appl. No.: 10/615,185

(22) Filed: Jul. 9, 2003

(65) Prior Publication Data

US 2005/0015864 A1 Jan. 27, 2005

(51) Int. Cl.⁷ .................................................. A61F 9/02
(52) U.S. Cl. ........................................................... 2/449
(58) Field of Search ............................... 2/10, 427, 431, 2/439, 449; 351/111, 41

(56) References Cited

U.S. PATENT DOCUMENTS

| | | | | |
|---|---|---|---|---|
| 5,000,558 A | * | 3/1991 | Blackstone | 351/41 |
| 5,379,463 A | * | 1/1995 | Schleger et al. | 2/431 |
| 5,426,473 A | * | 6/1995 | Riehm | 351/121 |
| 5,907,868 A | * | 6/1999 | Schleger et al. | 2/10 |

* cited by examiner

*Primary Examiner*—Katherine Moran
(74) *Attorney, Agent, or Firm*—Rosenberg, Klein & Lee

(57) ABSTRACT

Goggles includes a hard lens portion, and an soft upper protective member and a soft lower protective member combined with an upper edge and a lower edge of the lens portion, and two temples pivotally connected with two ends of the lens portion, convenient and comfortable to wear.

7 Claims, 8 Drawing Sheets

US 6,952,840 B2

GOGGLES

BACKGROUND OF THE INVENTION

1. Field of the Invention

This invention relates to goggles, particularly to ones convenient and comfortable to wear, and easily conforming to a wearer's face.

2. Description of the Prior Art

A Chinese proverb says eyes are the windows of a soul, and when people engage in work or activity, they will wear goggles to protect their eyes to prevent them from getting hurt.

A first kind of conventional goggles shown in FIG. 6, includes a hard lens portion 10, a soft protective portion 11 fitting around the lens portion 10, and a tying band 12 connected with the two opposite sides of the protective portion 11. The soft protective portion 11 around the hard lens portion 10 has its circumference to contact closely the face of a wearer so that the wearer can wear it comfortably. Nevertheless, The tying band 12 has to be positioned on the head, so it is not so convenient to put on and take off the head, and the hairstyle may be disfigured as well. At the same time, if the tying band 12 is tied too tight, the wearer may feel uncomfortable, and on the contrary, if it is tied too loose, the lens portion may not be kept stable on the head.

A second kind of conventional goggles shown in FIG. 7 includes a hard lens portion 20, a soft foam portion 21 fixed respectively on the upper and the lower edge of the lens portion 20, and a tying band 22 connected to the two opposite ends of the lens portion 20. The second conventional goggles have the same disadvantages as the first ones, and in addition, the soft foam members 21 have to be adhered with the upper and the lower edge of the lens portion 20, inconvenient to assemble as well as easily peeling off owing to the glue wetted after a long period of use to result in lack of closeness and comfort in wearing.

A third kind of conventional goggles shown in FIG. 8 includes a hard lens portion 30, a shield portion 31 extending to the upper, the lower, the right, and the left side of the lens portion 30, and two temples 32 respectively connected pivotally with two ends of the shield portion 31. This goggles is easy to wear because of the two foldable temples 32, and do not disfigure the hair style in wearing, but the shield portion 31 is made of hard material, uneasy to conform to the face of a wearer, not so comfortable to wear and not suitable for long time's wear.

SUMMARY OF THE INVENTION

The objective of the invention is to offer a kind of goggles having a soft protective member fitting with the upper and the lower edge of the lens portion and two temples connected pivotally with two ends of the lens portion, facilitating the goggles to be worn with convenience and comfort.

BRIEF DESCRIPTION OF THE INVENTION

This invention will be better understood by referring to the accompanying drawings, wherein.

DETAILED DESCRIPTION OF THE PREFERRED EMBODIMENTS

Figure 1:
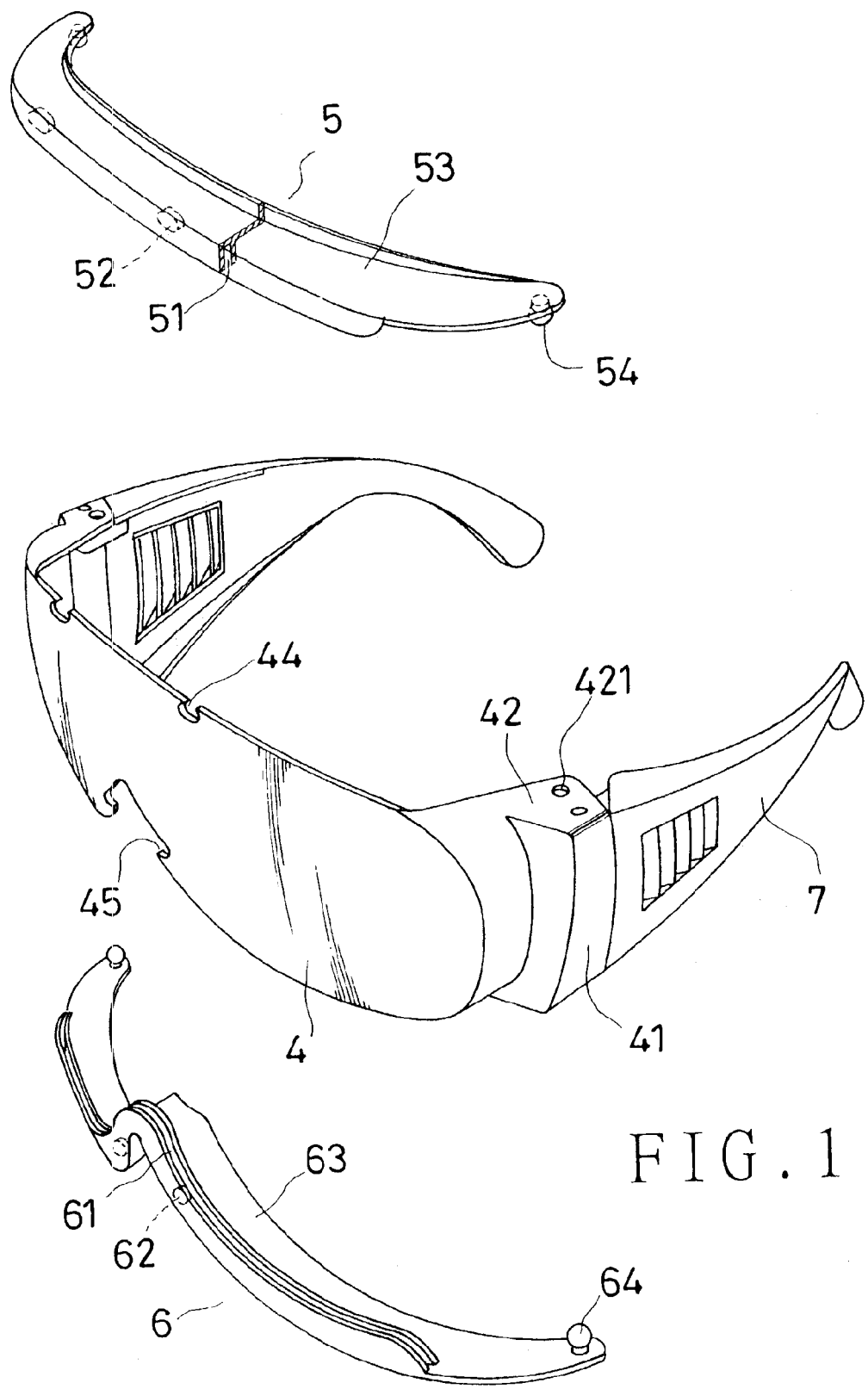
FIG. 1 is an exploded perspective view of a first embodiment of goggles in the present invention.
Figure 2:
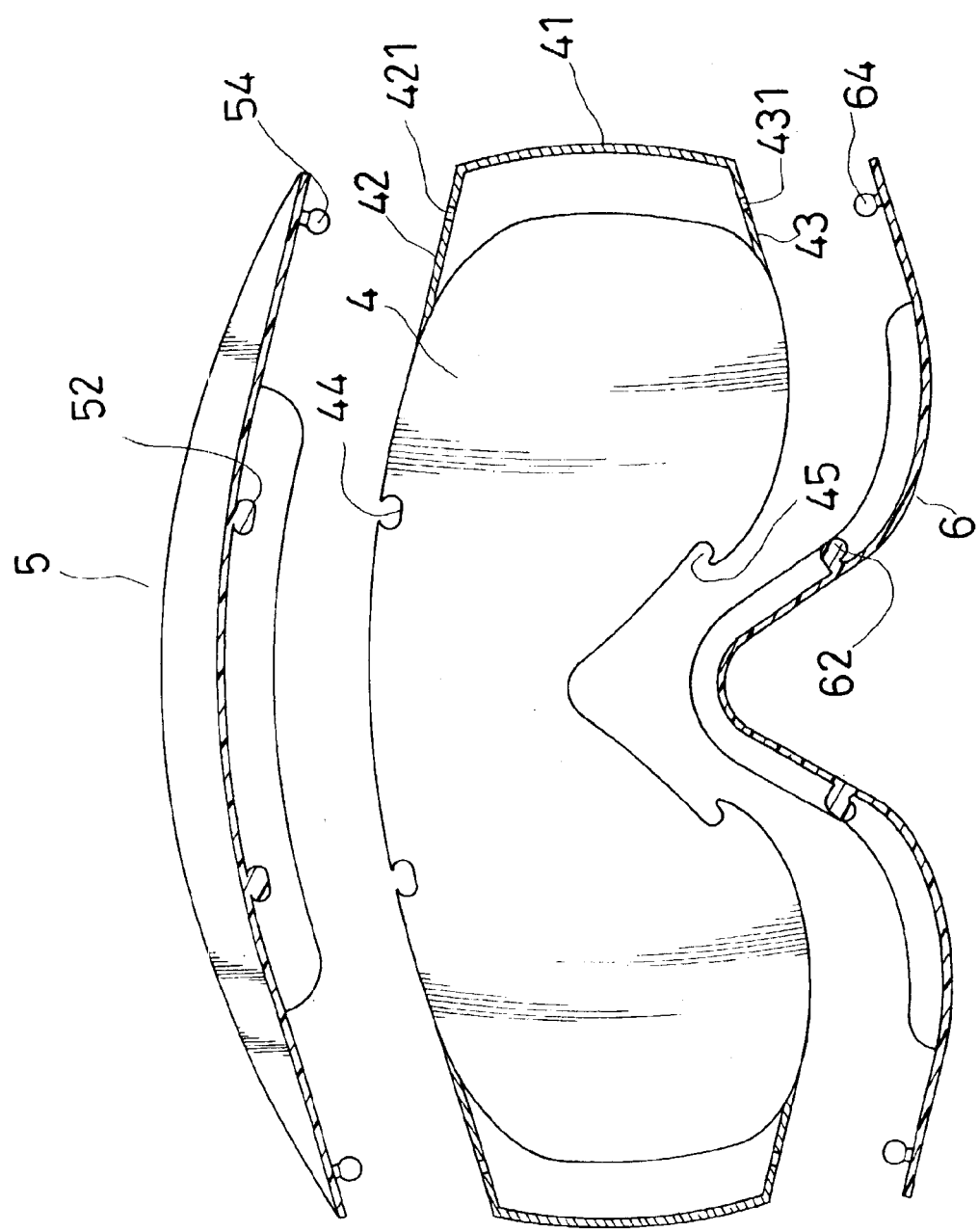
FIG. 2 is a front exploded view of the first embodiment of goggles in the present invention.

A first embodiment of goggles in the present invention, as shown in FIG. 1, includes a lens portion 4 made of hard material, two soft protective portions 5, 6 respectively combined with the upper edge and the lower edge of the lens portion 4, and two temples 7 to be supported on two ears are pivotally connected with the lens portion 4.

The lens portion 4 has an extension member 41 at two opposite sides pivotally connected with the two temples 7. Two combining members 42, 43 are respectively formed in an upper and a lower section of the extension member 41. Each combining member has a hooking hole 421, 431, and the lens portion 4 has two hooking grooves 44 spaced apart in the upper edge, and hooking grooves 45 face each other in the center section of the lower edge.

The soft upper protective member 5 has an elongate inverted U-shape groove 51 formed in the front side with its opening facing downward, two hooking projections 52 spaced apart in the groove 5 to hook with the hooking grooves 44 of the lens portion 4, a shield member 53 extending rearward from the upper end of the groove 51, two projections 54 provided downward at two ends of the shield member 53 to hook with the hooking holes 421 of the lens portion 4.

The soft lower protective member 6 has an elongate U-shape groove 61 formed in the front side with its opening facing upward, two projections 62 to correspond to and hook with the grooves 45 of he lens portion 4, a shield member 63 extending rearward from the bottom, and a projection 64 respectively on the two ends to fit with hooking hole 431 of the lens portion 4.

The two temples 7 are respectively connected pivotally with the extension members 41 at the two sides of the lens portion 4.

Figure 3:
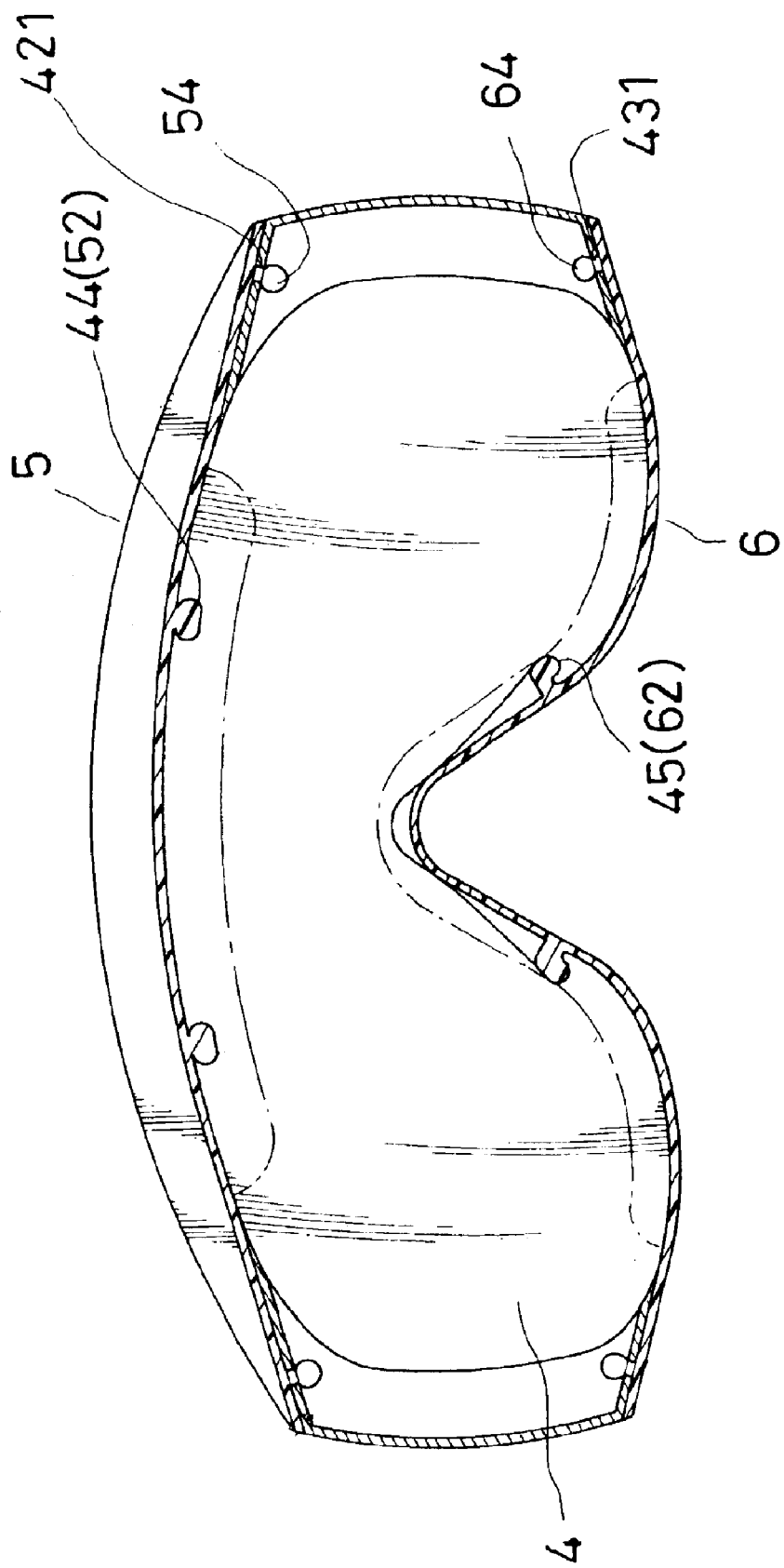
FIG. 3 is a front view of the first embodiment of goggles in the present invention.
Figure 4:
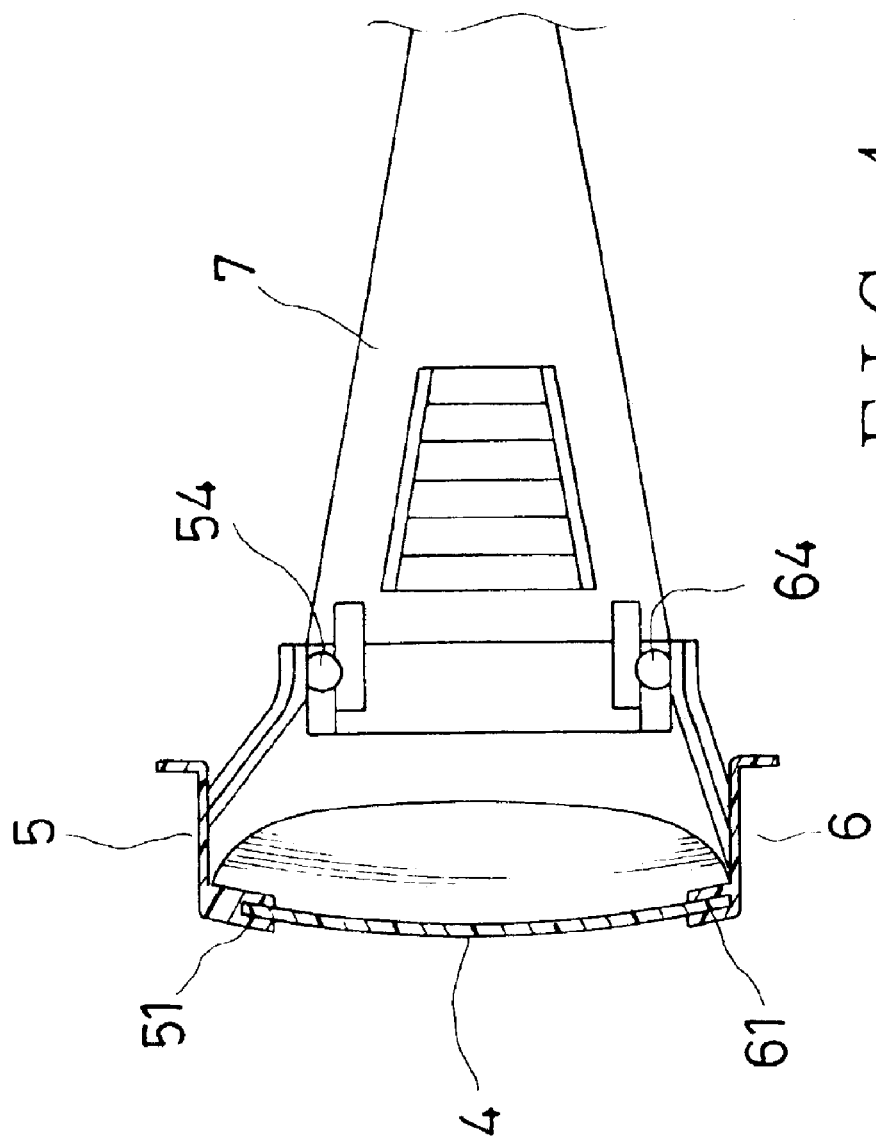
FIG. 4 is a partial side view of the first embodiment of goggles in the present invention.

In assembling, as shown in FIGS. 3 and 4, firstly, the temples 7 are directly connected pivotally with the extension members 41 at the two sides of the lens portion 4, and then the upper protective member 5 is combined with the lens portion 4, with the elongate grooves 51 fitting with the upper edge of the lens portion 4, and with the projections 54 inserting in the hooking holes 421 of the lens portion 4, assembling the upper protective member 5 with the lens portion 4 stably. Next, the lower protective member 6 is combined with the lens portion 4, with the elongate groove 61 fitting with the lower edge of the lens portion 4, with the hooking blocks 62 hooking with the hooking grooves 45, and with the projections 64 inserting in the hooking holes 431, assembling the lower protective member 6 with the lens portion 4 stably and finishing the assembly of the goggles.

As the hard lens portion 4 has the upper and the lower edge respectively attached with the upper and the lower soft protective member 5 and 6 for contacting the face of a wearer, the goggles can comparatively closely be worn by the wearer, so the wearer may feel comfortable. Besides, the temples 7 are also convenient for wearing, impossible to disfigure the hairstyle in wearing.

Figure 5:
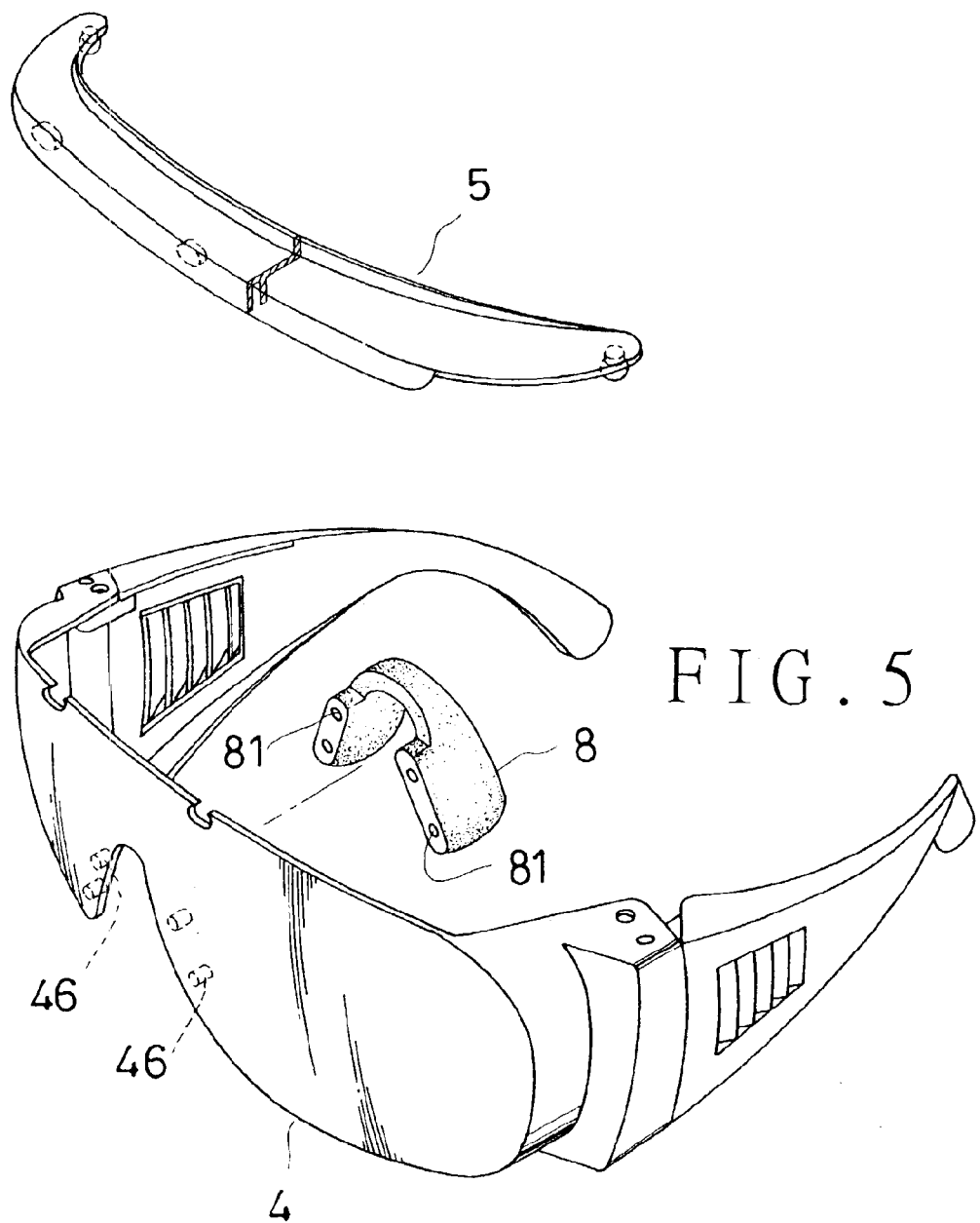
FIG. 5 is a second embodiment of goggles in the present invention.
Figure 6:
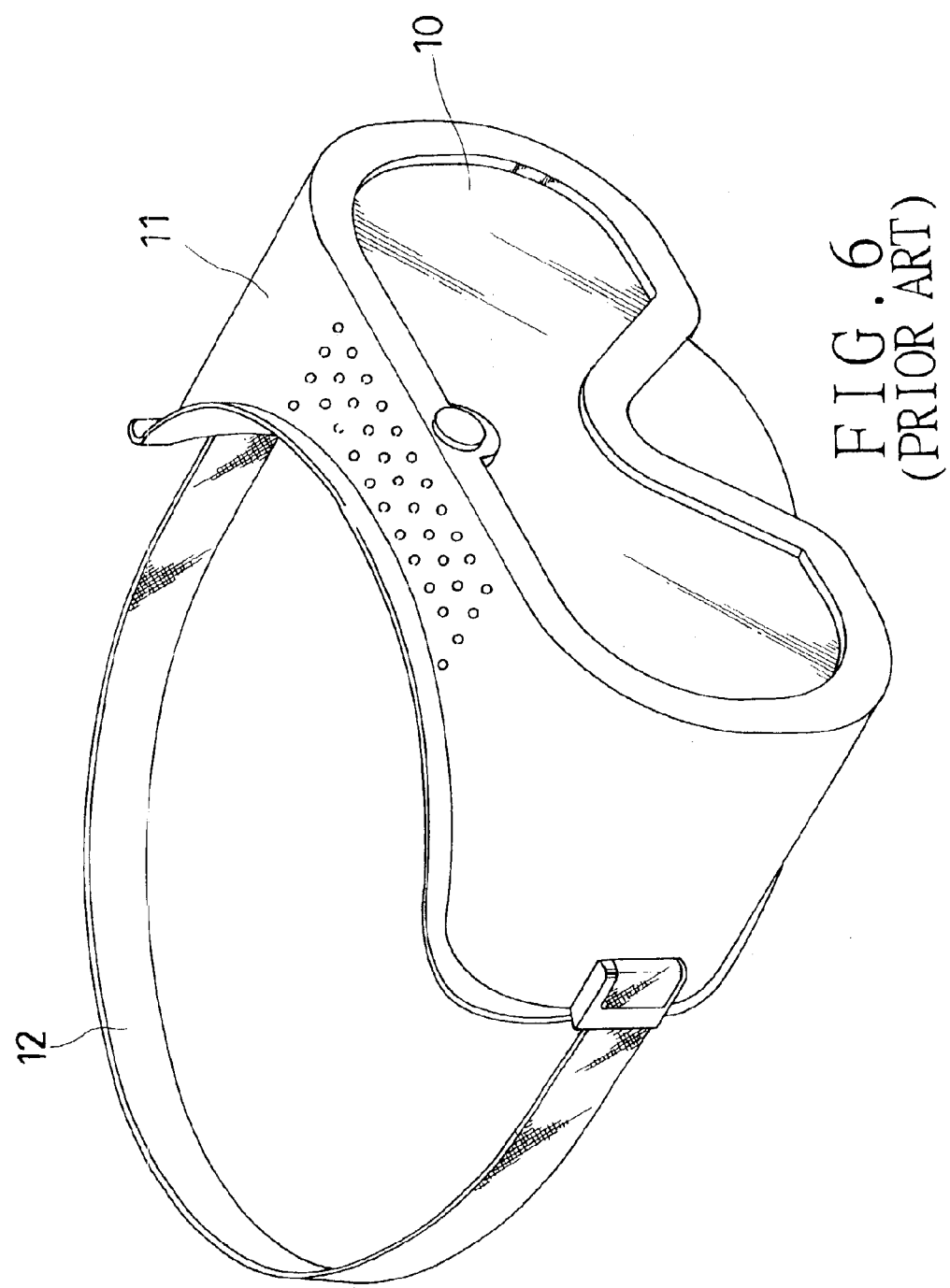
FIG. 6 is a perspective view of a first kind of conventional goggles.
Figure 7:
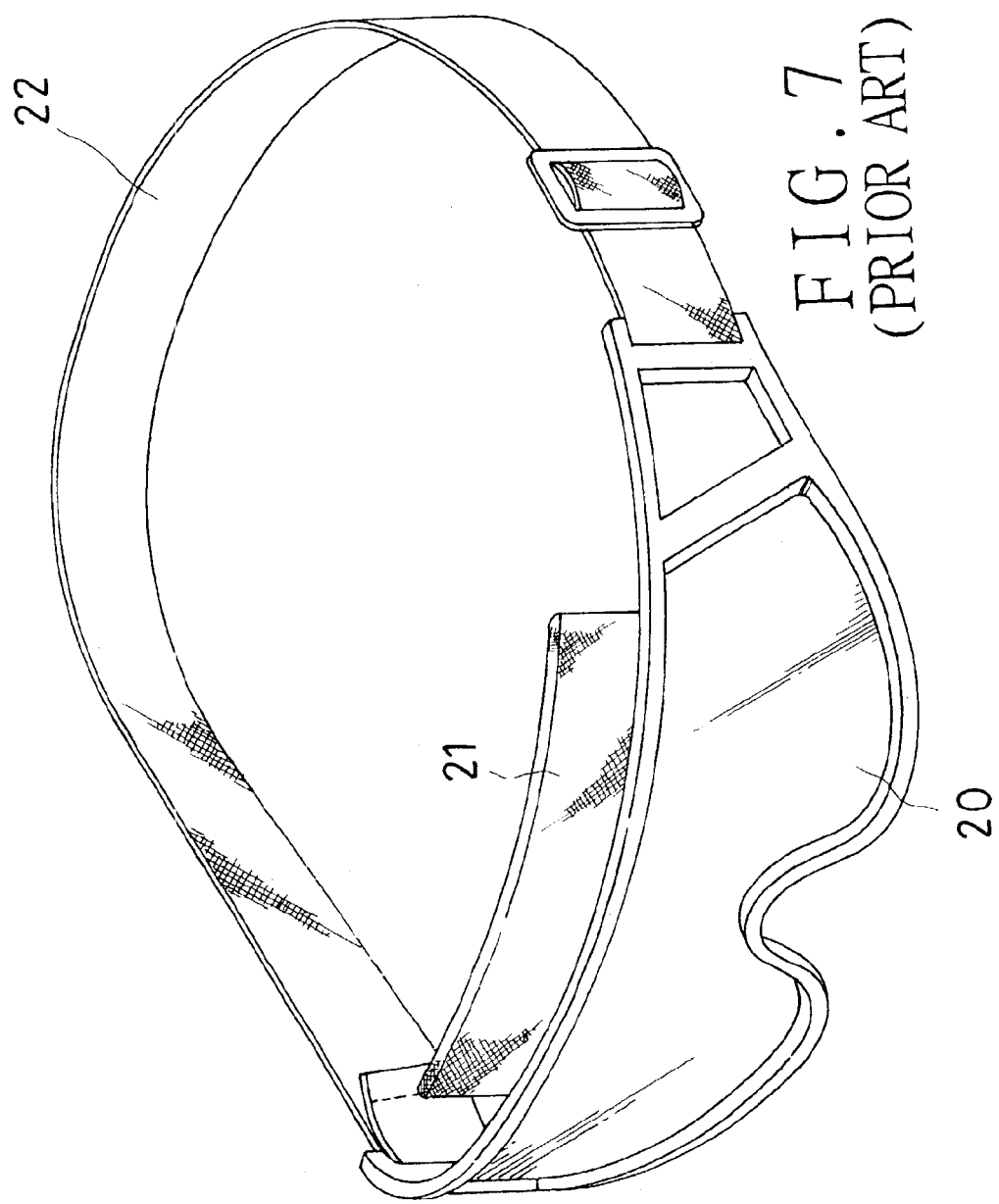
FIG. 7 is a perspective view of a second kind of conventional goggles.
Figure 8:
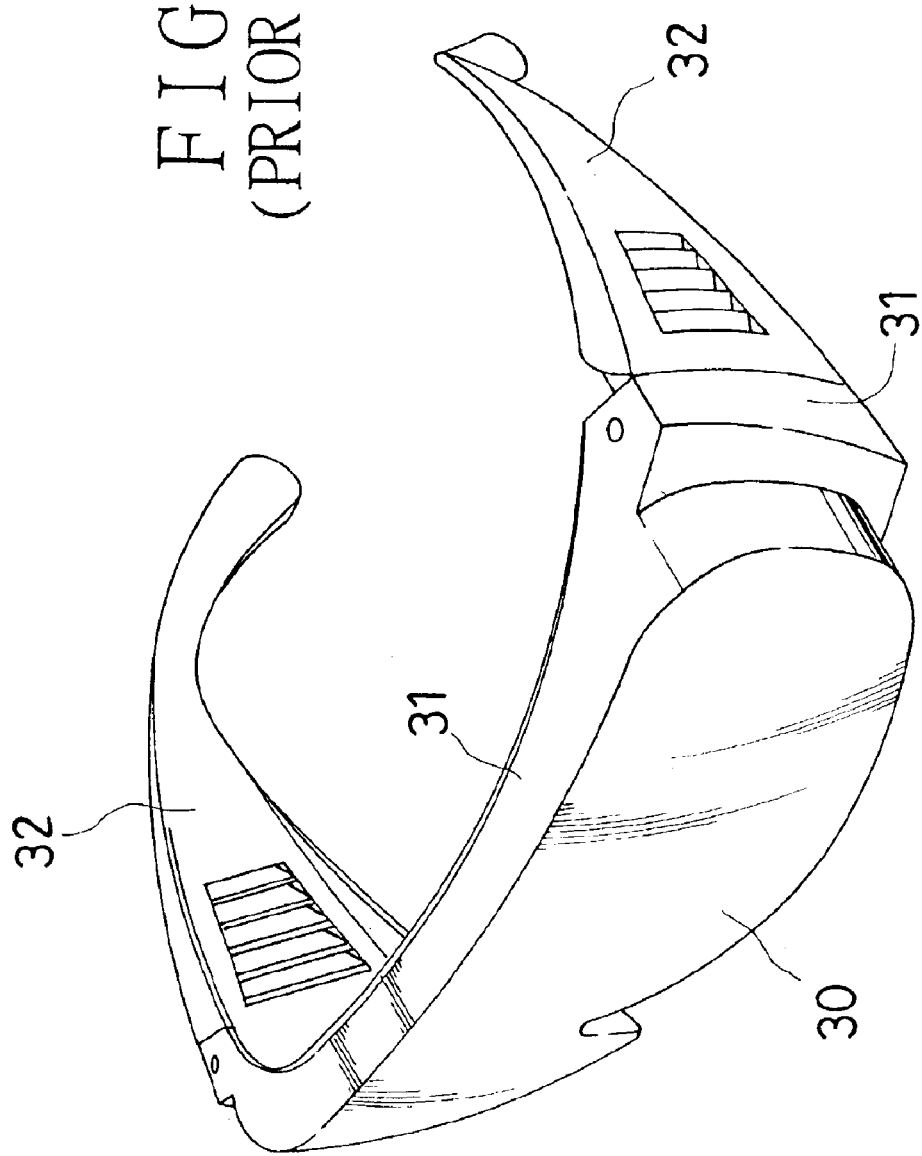
FIG. 8 is a perspective view of a third kind of conventional goggles.

A second embodiment of goggles in the invention shown in FIG. 5 includes a lens portion 4, an upper protective member 5 fixed on the upper edge of the lens portion 4, a soft nose pad 8 of an inverted U-shape fixed at the inner intermediate wall of the lens portion 4, plural small projections 46 respectively in the inner surface of the lens portion 4 at two sides of the nose pad 8 to fit with two holes 81 in two sides of the front surface of the nose pad 8 to combine the nose pad 8 with the lens portion 4.

While the preferred embodiments of the invention have been described above, it will be recognized and understood that various modifications may be made therein and the appended claims are intended to cover all such modifications that may fall within the spirit and scope of the invention.

What is claimed is:

1. Goggles comprising a hard lens portion, an upper soft protective member and two temples to be supported on the ears of a wearer, said upper soft protective member fixed with an upper edge of said lens portion, said temples combined with two ends of said lens portion; an extension member extending outward from the two ends of said lens portion, said extension members respectively having an upper flat combine member, said upper flat combine member having a hook hole, said lens portion having plural hook grooves each with an upper opening formed in the upper edge, said upper protective member having a projection in two ends of a shield portion extending rearward, said projections fitting in said hook holes of said extension members of said lens portion, said upper protective member having plural projections corresponding and fitting with said plural hook grooves of said lens portion, thus said upper protective member assembled with said lens portion to become goggles convenient and comfortable to wear.

2. The goggles as claimed in claim 1, wherein said upper protective member has an elongate groove to fit with the upper edge of said lens portion.

3. The goggles as claimed in claim 1, wherein a lower soft protective member is additionally provided to be combined with a lower edge of said lens portion.

4. The goggles as claimed in claim 3, wherein said two extension members of said lens portion have a flat combine member in a lower edge, and a hook hole in said combine member, said lens portion having two hook grooves at two sides of a center recess corresponding to a nose of a wearer, said lower protective member having a projection at two ends to fit in said hook holes of said lens portion, said lower protective member having two projections in an intermediate portion corresponding and fit with said hook grooves of said lens portion so as to combine said lens portion with said lower protective member stably.

5. The goggles as claimed in claim 4, wherein said lower protective member has an elongate groove to fit with the lower edge of said lens portion.

6. The goggles as claimed in claim 1, wherein said lens portion has its intermediate section corresponding to a nose provided with a nose pad.

7. The goggles as claimed in claim 6, wherein said lens portion has projections at two sides of the section corresponding to the nose of a wearer, and said nose pad has plural holes in a front side for said projections of said lens portion to fit with so as to stabilize said nose pad with said lens portion.

* * * * *